(12) United States Patent
Wilkinson et al.

(10) Patent No.: US 7,047,070 B2
(45) Date of Patent: May 16, 2006

(54) VALVED INTRADERMAL DELIVERY DEVICE AND METHOD OF INTRADERMALLY DELIVERING A SUBSTANCE TO A PATIENT

(75) Inventors: Bradley M. Wilkinson, North Haledon, NJ (US); Charles G. Hwang, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 189 days.

(21) Appl. No.: 10/112,756

(22) Filed: Apr. 2, 2002

(65) Prior Publication Data

US 2003/0187423 A1    Oct. 2, 2003

(51) Int. Cl.
*A61N 1/30* (2006.01)
*A61B 17/20* (2006.01)
*A61B 5/00* (2006.01)

(52) U.S. Cl. ............................ 604/20; 604/46; 600/573

(58) Field of Classification Search .................. 604/19, 604/22, 27, 28, 30, 46, 48, 500, 506, 507, 604/93.01, 115–117, 131–134, 167.01, 167.03, 604/167.05, 174, 176, 179–181, 186, 187, 604/192, 212, 239, 246–248, 264, 272, 274, 604/289, 290, 173, 20, 191; 600/362, 378, 600/383, 573; 606/131, 132, 167, 172, 181–183, 606/185–189

See application file for complete search history.

(56) References Cited

U.S. PATENT DOCUMENTS

| | | | |
|---|---|---|---|
| 3,595,231 A * | 7/1971 | Pistor ......................... 604/173 |
| 3,964,482 A | 6/1976 | Gerstel et al. |
| 5,250,023 A | 10/1993 | Lee et al. |
| 5,279,544 A | 1/1994 | Gross et al. |
| 5,320,600 A | 6/1994 | Lambert |
| 5,389,070 A * | 2/1995 | Morell ........................ 604/506 |
| 5,527,288 A | 6/1996 | Gross et al. |
| 5,656,032 A | 8/1997 | Kriesel et al. |
| 5,735,818 A | 4/1998 | Kriesel et al. |
| 5,879,326 A | 3/1999 | Godshall et al. |
| 5,997,501 A | 12/1999 | Gross et al. |
| 6,048,337 A | 4/2000 | Svedman |

(Continued)

FOREIGN PATENT DOCUMENTS

CA    2350307    1/2002

(Continued)

OTHER PUBLICATIONS

Mark R. Prausnitz, "Drug Delivery by Electrical, Ultrasonic, and Microneedle Disruption of Biological Barriers", Abstracts of Papers of the American Chemical Society, Mar. 26, 2000:219:716 MEDI.

(Continued)

*Primary Examiner*—Nicholas D. Lucchesi
*Assistant Examiner*—Roz Maiorino
(74) *Attorney, Agent, or Firm*—Robert E. West

(57) ABSTRACT

An intradermal delivery device for delivery a substance into the skin of a patient has a fluid chamber for containing the substance, at least one micro skin penetrating member, and a valve controlling the flow of the substance from the fluid chamber to the micro skin penetrating member. An adhesive releasably attaches the device to the skin of the patient, the fluid chamber can be sized to hold a unit dose of the substance, and, in some embodiments, the fluid chamber can be releasably coupled to a housing of the device.

40 Claims, 8 Drawing Sheets

U.S. PATENT DOCUMENTS

| | | | |
|---|---|---|---|
| 6,050,988 | A | 4/2000 | Zuck |
| 6,083,196 | A | 7/2000 | Trautman et al. |
| 6,132,755 | A * | 10/2000 | Eicher et al. ............ 424/427 |
| 6,186,982 | B1 | 2/2001 | Gross et al. |
| 6,219,574 | B1 * | 4/2001 | Cormier et al. ............ 604/20 |
| 6,230,051 | B1 | 5/2001 | Cormier et al. |
| 6,256,533 | B1 | 7/2001 | Yuzhakov et al. |
| 6,261,272 | B1 | 7/2001 | Gross et al. |
| 6,322,808 | B1 | 11/2001 | Trautman et al. |
| 6,440,096 | B1 * | 8/2002 | Lastovich et al. ............ 604/27 |
| 6,558,361 | B1 * | 5/2003 | Yeshurun ............ 604/272 |
| 6,565,532 | B1 * | 5/2003 | Yuzhakov et al. ............ 604/142 |
| 6,623,457 | B1 * | 9/2003 | Rosenberg ............ 604/191 |
| 6,656,147 | B1 * | 12/2003 | Gertsek et al. ............ 604/28 |
| 2002/0006355 | A1 | 1/2002 | Whitson |

FOREIGN PATENT DOCUMENTS

| | | |
|---|---|---|
| GB | 2 221 394 | 2/1990 |
| WO | WO 96/37256 | 11/1996 |
| WO | WO 97/03718 | 2/1997 |
| WO | WO 97/48440 | 12/1997 |
| WO | WO 97/48441 | 12/1997 |
| WO | WO 00/12173 | 3/2000 |
| WO | WO 00/74766 | 12/2000 |

OTHER PUBLICATIONS

Devin V. McAllister et al., "Microfabricated Microneedles For Gene And Drug Delivery", Annual Review of Biomedical Engineering, 2000, pp. 289/313.

Liwei Lin et al., "Silicon/Processed Microneedles", Journal of Microelectromechanical Systems, Mar. 1999, pp. 78/84, vol. 8, No. 1.

Ljubomir Ilic et al., "Microfabrication of Individual 200 μm Diameter Transdermal Microconduits Using High Voltage Pulsing in Salicylic Acid and Benzoic Acid", Journal of Investigative Dermatology, Jan. 2001, pp. 40/49, vol. 116, No. 1.

Sebastien Henry et al., "Microfabricated Microneedles: A Novel Approach to Transdermal Drug Delivery", Journal of Pharmaceutical Sciences, Aug. 1998, pp. 922/925, vol. 87, No. 8.

John Brazzle et al., "Micromachined Needle Arrays for Drug Delivery or Fluid Extraction", IEEE Engineering in Medicine and Biology, Nov./Dec. 1999, pp. 53/58.

* cited by examiner

VALVED INTRADERMAL DELIVERY DEVICE AND METHOD OF INTRADERMALLY DELIVERING A SUBSTANCE TO A PATIENT

FIELD OF THE INVENTION

The present invention relates to an intradermal delivery device having a fluid chamber to contain a substance to be delivered intradermally to a patient in a target area of the skin. The present invention also relates to a method of delivering a substance into the skin of a patient.

BACKGROUND OF THE INVENTION

Drugs and pharmaceutical agents are delivered to patients by a variety of methods. A typical method delivers the drug or pharmaceutical agent subcutaneously by a stainless steel cannula. Although the subcutaneous sampling and delivery methods using a cannula are effective for many applications, the pain normally induced by the cannula has prompted the development of less painful delivery methods.

The skin is made up of several layers, with the upper composite layer being the epithelial layer. The outermost layer of the skin, the stratum corneum, is a waterproof membrane with well known barrier properties that prevent the influx of undesirable molecules and various foreign substances while preventing the outflux of various analytes. The stratum corneum is a complex structure of compacted keratinized cell remnants having a thickness of about 10–30 microns.

The natural impermeability of the stratum corneum prevents the administration of most pharmaceutical agents and other substances through the skin. Numerous methods and devices have been proposed to enhance the permeability of the skin and to increase the diffusion of various drugs through the skin for utilization by the body. Typically, the delivery of drugs through the skin is enhanced by increasing either the permeability of the skin or the force or energy used to direct the drug through the skin.

Another method of sampling and delivering various substances through the skin is by forming micropores or cuts through the stratum corneum. By piercing the stratum corneum and delivering a drug to the skin in or below the stratum corneum, many drugs can be administered effectively. In a similar manner, some substances can be extracted from the body through cuts or pores formed in the stratum corneum. The devices for piercing the stratum corneum generally include a plurality of micron size needles or blades having a length to pierce the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

The above-noted devices that include micron-sized needles or blades can be effective in delivering substances to the body. However, these needles and blades having a length of a few microns to a few hundred microns typically do not penetrate skin to a uniform depth. The natural elasticity and resilience of the skin will often result in the skin being deformed by the needles rather than pierced. A microneedle array when pressed against the skin often results in the outermost needles penetrating the skin while the innermost needles do not penetrate or only penetrate to depth less than the outermost needles.

The prior methods and devices for the intradermal administration of substances have exhibited limited success. Accordingly, an unmet need exists in the industry for an improved device for the sampling and administration of various drugs and other substances to the body.

SUMMARY OF THE INVENTION

The present invention is directed to a method and device for the intradermal sampling or delivery of a substance into the skin of a patient. More particularly, the invention is directed to a method and device for controlling the flow of a pharmaceutical agent, such as a drug or vaccine, through the device for delivery into or below the stratum corneum of the skin to a depth sufficient for the pharmaceutical agent to be absorbed and utilized by the body.

Accordingly, it is an object of the invention to provide a sampling or delivery device having at least one skin penetrating member having a length that provides an increased comfort level to the patient.

A further object of the invention is to provide a method of penetrating the skin for sampling or delivering a substance through the skin substantially without pain to the patient.

Another object of the invention is to provide a delivery device having a plurality of micro skin penetrators, such as microtubes, needles, microneedles, blades or lancets, selected for piercing the stratum corneum of the skin to a depth that is short of the nerve endings.

Still another object of the invention is to provide a delivery device having a manually operated valve to control the delivery of a substance to the at least one micro skin penetrating member of the delivery device.

A further object of the invention is to provide a pre-filled delivery device having a reservoir containing a substance, at least one micro skin penetrating member, and a reservoir outlet for supplying a substance to the micro skin penetrating member for delivery to the patient.

Another object of the invention is to provide a delivery device having a reservoir containing a substance to be delivered to a patient, wherein the reservoir is defined, at least in part, by a movable wall that is depressed to dispense the substance to the patient.

Still another object of the invention is to provide a delivery device having at least one micro skin penetrating member for delivering a substance to a target area on the skin of a patient and a ridge encircling the micro skin penetrating members to form a containment area around the target area.

These and other aspects of the invention are substantially achieved by providing a device for delivering a substance into the skin of a patient. The device comprises a housing having a fluid chamber having an outlet. A valve member is coupled to the housing for controlling the flow of the substance through the outlet of the chamber. A skin penetrating device is coupled to the housing and is in fluid communication with the fluid chamber for delivering the substance to the patient.

The objects and advantages of the invention are further attained by providing a device for intradermally delivering a substance to a patient. The device comprises a housing having a bottom face dimensioned to contact the skin of the patient. The housing has a fluid chamber with an outlet, and a manually operated valve coupled to the housing for controlling the flow of the substance through the outlet of the chamber. A micro skin penetrating member is coupled to the housing and is in fluid communication with the chamber. An arrangement is provided for applying to the substance a pressure sufficient to deliver the substance into the skin of a patient.

A yet further object of the invention is to provide a method for delivering a substance into or through the skin of a patient. The method comprises positioning on the skin of a patient a delivery device including a housing; a fluid chamber on the housing for containing the substance, said chamber having an outlet for the substance; a valve member connected to said housing to control the flow of the substance through the outlet; and a skin penetrating device on the housing and in fluid communication with the chamber for delivering the substance into the skin of the patient. A sufficient pressure is applied for the micro skin penetrating members to penetrate the skin to a depth sufficient to deliver the substance to the patient. The valve is opened, the substance is introduced from the fluid chamber to the micro skin penetrating members under pressure, and the substance is delivered to the patient. In some embodiments, the fluid chamber is removably coupled to the housing before the delivery device is positioned on the skin.

The aspects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

Figure 1:
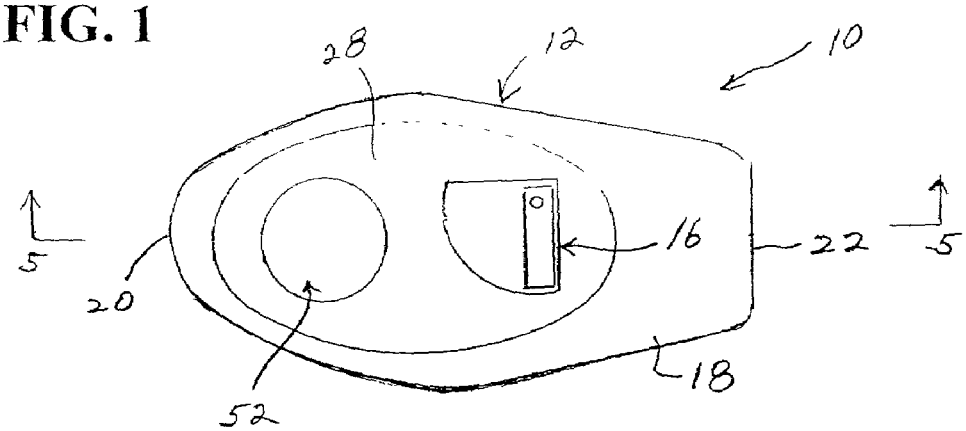
FIG. 1 is a top plan view of the device in accordance with a first embodiment of the invention for delivering a substance into the skin of a patient.
Figure 2:
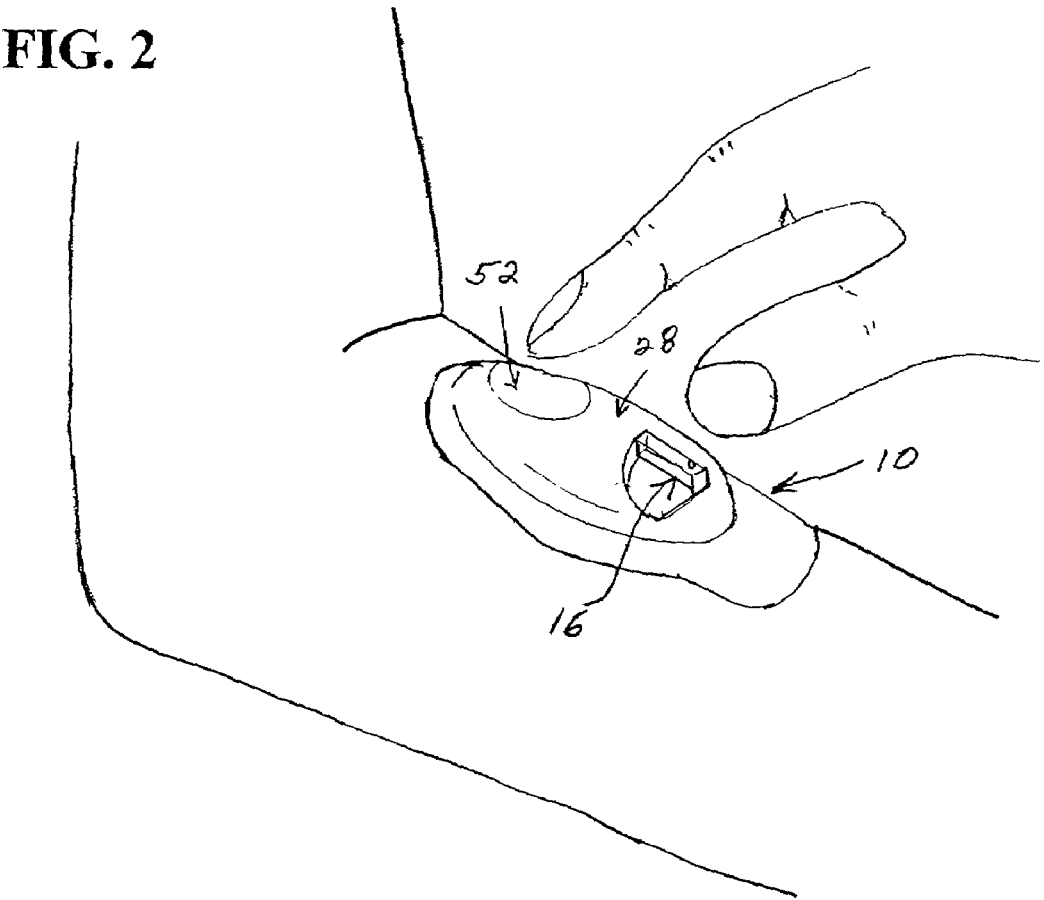
FIG. 2 is a perspective view of the device of FIG. 1 showing the device on the skin of a patient.
Figure 3:
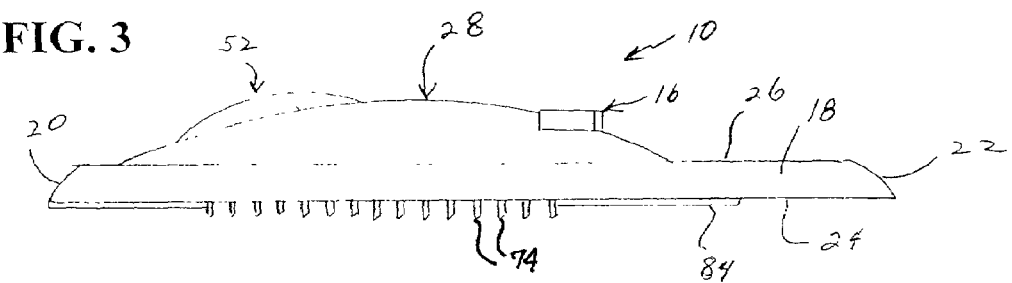
FIG. 3 is a side elevational view of the device of FIG. 1 showing the micro skin penetrating members extending from the bottom face of the device.

The present invention is directed to a device for sampling, monitoring or delivering a substance into the skin of a patient. More particularly, the invention is directed to a delivery device and to a method for administering a substance to below the stratum corneum of the skin of a patient.

As used herein, the term "penetrate" refers to entering a layer of the skin without passing completely through. The term "pierce" refers to passing completely through a layer of the skin.

The device and method of the present invention are suitable for use in administering various substances, including pharmaceutical agents, to a patient, and especially to a human patient. As used herein, a pharmaceutical agent includes a substance having biological activity that can be delivered through the body membranes and surfaces, and particularly into the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The device of the invention is primarily for delivering a substance into selected layers of the skin. In alternative embodiments of the invention, the device is suitable for withdrawing a substance or monitoring the level of a substance in the body. Examples of substances that can be monitored or withdrawn include blood, interstitial fluid or plasma that can then be analyzed for analytes, glucose, drugs and the like.

Referring to FIGS. 1–7, the invention in a first embodiment is directed to a device 10 having a supporting body 12 with a skin penetrating device 14 and a valve assembly 16. Device 10 is constructed for penetrating one or more selected layers of the dermis of a patient to attain the desired depth of penetration. The desired depth of penetration is determined by the substance being delivered, the delivery rate and the absorption rate. Penetration to a depth of 1 mm results in a high uptake by the body. Penetration to a depth on the order of 5 mm would slow delivery. The device is provided with one or more penetrating members each having a length to pierce the stratum corneum substantially without penetrating the dermis, which is below the stratum corneum and below the other layers of the epidermis. By delivering a substance to just below the stratum corneum, the substance can be absorbed and utilized by the body substantially without pain or discomfort to the patient. The device penetrates the dermis to a depth without contacting pain inducing nerves in the skin. Each penetrating member has a length sufficient to pierce the stratum corneum to a depth at which pain is reduced or minimized and the substance is absorbed by the body.

Referring to the drawings, body 12 forms a housing that has a generally flat profile when attached to the skin of a patient. The flat profile provides an ease of attachment to the skin and less obstruction to the patient. As shown in the embodiment of FIG. 1, body 12 has an elongated shape, although in alternative embodiments, body 12 can have a circular, square, rectangular or other shape.

As shown in FIG. 1, body 12 includes a base 18 having a generally elongated configuration. In this embodiment, base 18 has a generally planar shape with a rounded front end 20 and a straight rear end 22. Base 18 has a substantially flat bottom face 24 and a top face 26. A reservoir 28 is defined on the top face 26 of base 18 for containing a substance to be delivered to the patient as discussed hereinafter in greater detail.

Figure 4:
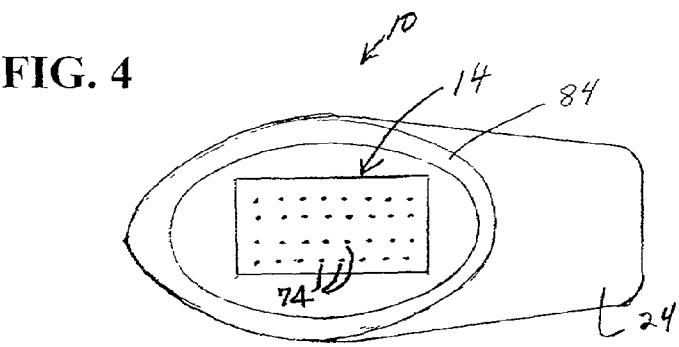
FIG. 4 is a bottom plan view of the device of FIG. 1 showing the micro skin penetrating members.
Figure 5:
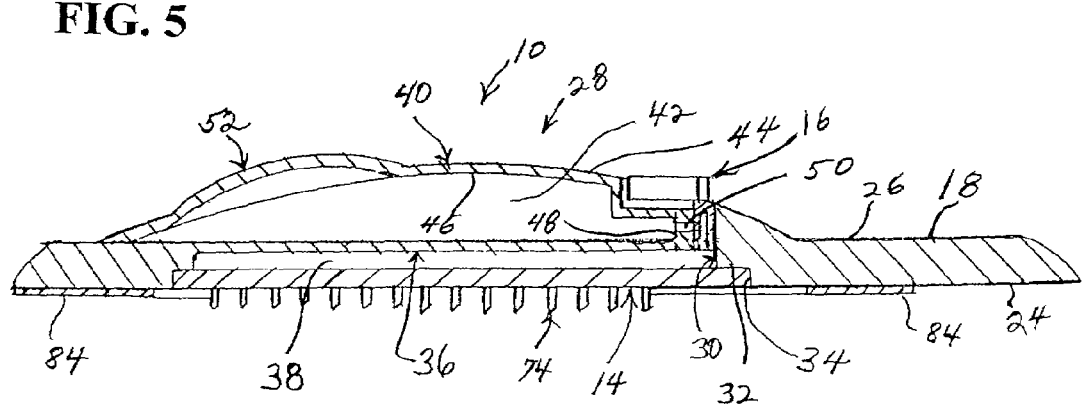
FIG. 5 is a cross-sectional side view of the device of FIG. 1 taken along line 5—5 of FIG. 1 showing the fluid chamber, the cavity and the control valve.

Base 18 is dimensioned and configured to be placed against the skin of a patient for delivering a substance such as a drug or pharmaceutical. As shown in FIGS. 4 and 5, base 18 has a recess 30 dimensioned to receive skin penetrating device 14. Recess 30 includes a ledge 32 and a side wall 34 for supporting skin penetrating device 14. Side wall 34 preferably has a height sufficient to receive skin penetrating device 14 such that the outer face of skin penetrating device 14 lies in the plane of bottom face 24 of base 18. Ledge 32 has a width sufficient to support skin penetrating device 14. As shown in FIG. 4, recess 30 has a dimension complementing the outer dimension of skin penetrating device 14 so that skin penetrating device 14 can be coupled to base 18. In preferred embodiments, skin penetrating device 14 is coupled to base 18 by a suitable adhesive. In other embodiments, skin penetrating device 14 can be integrally formed with base 18. Other coupling arrangements can also be used.

Referring to FIG. 5, base 18 includes a top wall 36 overlying recess 30. Recess 30 has a depth extending between top wall 36 and bottom face 24 of base 18 that is greater than the thickness of skin penetrating device 14. Recess 30 forms a cavity 38 between top wall 36 and skin penetrating device 14. Cavity 38 is dimensioned to allow the flow of a liquid while providing a volume to minimize the dead space in base 18.

Reservoir 28 has an outer wall 40 integrated with the body 12 and spaced from top wall 36 of base 18 to define an internal chamber 42. Chamber 42 is dimensioned to contain a sufficient volume, for example, a predetermined unit dose, of a substance to be delivered to a patient. The chamber 42 is prefilled with the substance. In the embodiment illustrated, outer wall 40 of reservoir 28 has a generally dome shape with a convex outer surface 44 and a concave inner surface 46. Outer wall 40 is coupled to top face 26 of base 18 by a suitable adhesive or a weld to form a fluidtight seal for enclosing reservoir 28.

Reservoir 28 includes an end wall 48 having a channel 50 extending between cavity 38 and chamber 42, the channel 50 defining an outlet of the chamber 42. Outer wall 40 includes a movable dispensing member 52 for applying sufficient pressure to the chamber 42 to dispense a substance from chamber 42 through channel 50 to cavity 38. In the embodiment illustrated, dispensing member 52 is a flexible member that can be depressed inwardly toward chamber 42 to dispense the substance. Dispensing member 52 initially has a concave inner surface 54 to form a generally bubble shape. Preferably, dispensing member 52 is made of a resilient, flexible plastic material that can be depressed and deflected inward by manual pressure by the user. In this embodiment, outer wall 40 is substantially rigid.

Figure 6:
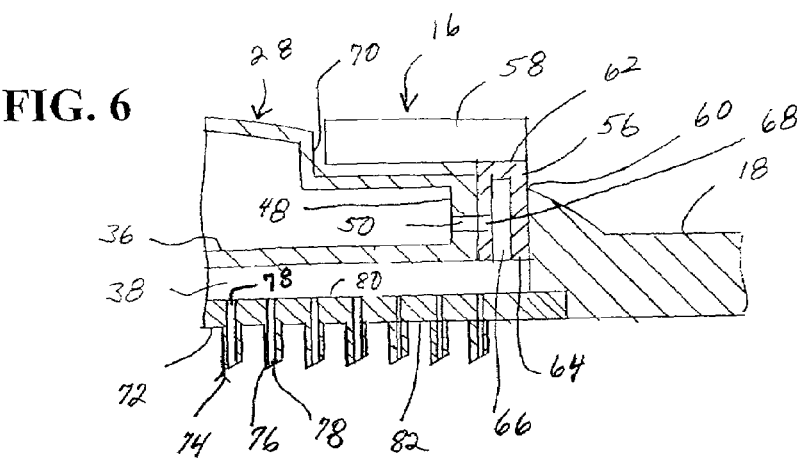
FIG. 6 is an enlarged cross-sectional view of the control valve.

Valve assembly 16 is positioned in channel 50 to control the flow of the substance from chamber 42 through channel 50. In this embodiment, valve assembly 16 is a rotatable valve having a valve element, or valve body 56, having a portion exposed to the exterior of the delivery device 10 for manipulation between a closed position and an open position. In the illustrated embodiment, the exposed portion has an actuator handle 58. Referring to FIG. 6, valve body 56 has a substantially cylindrical shape for rotating within aperture 60 in base 12. Aperture 60 has a shape and dimension complementing valve body 56 and extends from top face 26 of base 18 to cavity 38. As shown in FIG. 6, handle 58 is coupled to a top end 62 of valve body 56. Valve body 56 has a lower end 64 positioned at the opening to cavity 38. The exposed portion of the valve body 56 serves as an indicator indicating whether the valve body is in a closed position or an open position. For example, as can be appreciated from FIGS. 2 and 6, pointing of the handle 58 in the longitudinal direction of the delivery device 10 indicates that the valve body 56 is open. On the other hand, as can be seen from FIGS. 1 and 6, pointing of the handle 58 in the transverse direction of the delivery device 10 indicates that the valve body 56 is closed.

Valve body 56 includes an axial passage 66 extending from lower end 64. A radial passage 68 extends through valve body 56 and intersects axial passage 66. Radial passage 68 is aligned with channel 50 in end wall 48 of reservoir 28 to provide fluid communication between reservoir 28 and cavity 38. Valve body 56 is rotatable within aperture 60 as depicted in FIG. 1 to open and close valve assembly 16. In the embodiment illustrated, a recess 70 is provided in top face 26 of base 18 to receive handle 58 of valve assembly 16. Recess 70 allows handle 58 to rotate about 90° from the closed position shown in FIG. 1 to the open position shown in FIG. 6.

Referring to FIG. 6, skin penetrating device 14 includes a base 72 having at least one micro skin penetrating member 74 extending outwardly from base 72. In the illustrated embodiment, there are a plurality of micro skin penetrating members 74 arranged in an array of spaced apart rows and columns, as can best be appreciated from FIG. 4.

In the illustrated embodiment, micro skin penetrating members 74 are hollow needles each having a beveled tip 76 for penetrating the skin of a patient and an axial passage 78 extending between tip 76 and a top face 80 of base 72. Base 72 has a bottom face 82 supporting micro skin penetrating members 74. Preferably, bottom face 82 of base 72 has a substantially planar configuration and is oriented in the plane of bottom face 24 of base 18.

Skin penetrating device 14, having at least one micro skin penetrating member 74, can be made from various materials. In one embodiment, a plurality of micro skin penetrating members 74 are spaced apart from each other a uniform distance and have a uniform length. The skin penetrating device 14 is made from silicon by, for example, suitable silicon etching or micromachining steps. In other embodiments, device 14 is made from stainless steel, tungsten steel, or alloys of nickel, molybdenum, chromium, cobalt and titanium. Alternatively, the micro skin penetrating members can be made of ceramic materials, polymers and other non-reactive materials.

The micro skin penetrating members 74 have a length suitable to achieve the desired depth of penetration in the skin. The length and thickness of the micro skin penetrating members 74 are selected based on the substance being administered or withdrawn and the thickness of the skin in the location where the device is to be applied. The micro skin penetrating members can be microneedles, microtubes, solid or hollow needles, lancets and the like. Generally, the micro skin penetrating members have a length, measured from the base to the tip of the member, of about 50 microns to about 4,000 microns and preferably, about 250 microns to 1,000 microns. The needles are typically mounted in a suitable base and have a substantially uniform length. In some embodiments, the micro skin penetrating members are about 30-gauge to about 50-gauge needles having a length of about 500 microns to about 1,000 microns. The micro skin penetrating members have a substantially square cross-sectional shape. Alternatively, the micro skin penetrating members can be triangular, cylindrical, or pyramid-shaped, or they can be flat blades.

The skin penetrating members 74 can be in an array covering an area of from about one cm$^2$ to about 10 cm$^2$. The array can have a width and length of about one centimeter to about five centimeters. The base 40 has a thickness of about 200 to 400 microns, and typically about 250 microns.

Generally, when the device is used as a delivery device, a pharmaceutical agent or drug solution is provided in the reservoir 28. In alternative arrangements, a dried or lyophilized drug or pharmaceutical agent can be provided in the cavity 38 or in the axial passages 78 of the skin penetrating member 74. A diluent such as distilled water or saline solution can be provided in the reservoir 28 and selectively allowed to flow by manipulation of the valve handle 58 into the cavity 38 and the axial passages 78 of the micro skin penetrating members 74 to dissolve and reconstitute the drug or pharmaceutical agent and then deliver the drug to the patient.

Bottom face 24 of base 18 in the embodiment of FIGS. 1–7 includes a pressure sensitive adhesive 84 surrounding skin penetrating device 14. Preferably, adhesive 84 forms a continuous circle around skin penetrating device 14 and has an area sufficient to releasably attach device 10 to the surface of a patient's skin. In all embodiments of the invention, a protective cover can be coupled to bottom face 24 of base 18 to cover adhesive 84 and skin penetrating device 14 until ready for use. The cover can be a rigid member or a flexible sheet material that can be peeled from the adhesive 84.

Figure 7:
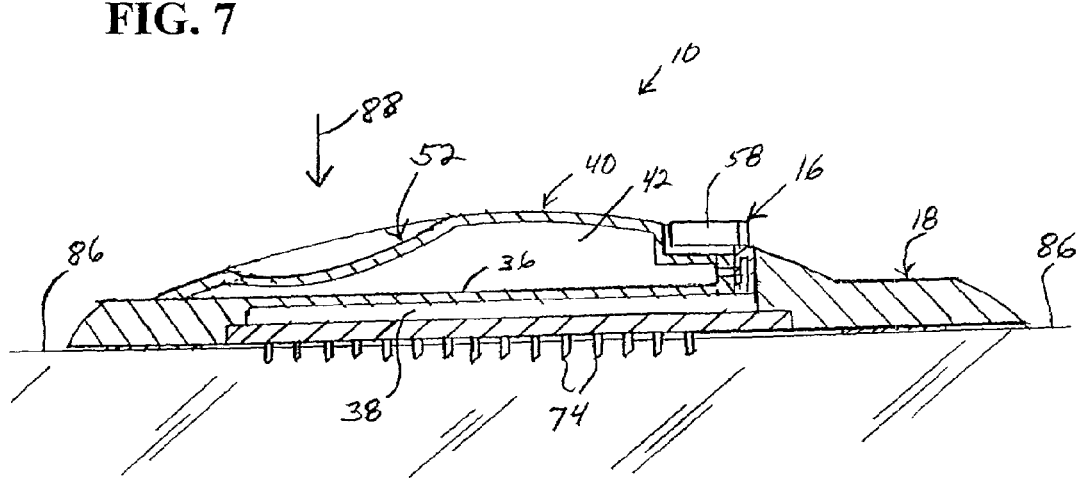
FIG. 7 is a cross-sectional side view similar to FIG. 5 but showing the device in contact with the skin of a patient and dispensing the substance to the patient.

Device 10 is primarily intended to be a prefilled delivery device containing a pharmaceutical agent or drug to be delivered to a patient. In use, device 10 is removed from its protective packaging and positioned on the surface of skin 86 as shown in FIG. 7. A downward pressure is applied against body 12 with a force sufficient to cause micro skin penetrating members 74 to penetrate skin 86 to a desired depth, as determined by the length of skin penetrating members 74. Adhesive 84 attaches device 10 to the surface of skin 86 to prevent lateral movement of device 10 during delivery of the substance contained within reservoir 28. Adhesive 84 also forms a seal to prevent leakage of the substance from a target area of skin 86 penetrated by micro skin penetrating members 74.

After device 10 is positioned on skin 86, valve assembly 16 is rotated to the open position shown in FIGS. 6 and 7 to provide fluid communication between chamber 42 of reservoir 28 and cavity 38 of base 18. The position of the valve handle 58 indicates whether the valve is open or closed. A manual pressure is applied against dispensing member 52 as indicated by arrow 88 in FIG. 7 to deflect dispensing member 52 inwardly into chamber 42, thereby imposing a dispensing pressure on the substance in the chamber. The dispensing pressure forces the substance from chamber 42 through channel 50 and valve body 66 to cavity 38 where the substance can flow through the axial passages 78 of skin penetrating members 74. The dispensing pressure and the substance is accordingly dispensed so long as so long as the dispensing member 52 is depressed; and the dispensing pressure is gradually released upon release of the dispensing member 52. The manual pressure is maintained for a time sufficient to enable a sufficient amount of the substance to be delivered to a desired depth in the skin 86 where the substance can be absorbed and utilized by the body. Manual pressure is maintained throughout the delivery operation.

Device 10, including body 12 and valve assembly 16, is preferably made of a polymeric material that is non-reactive with the substance being delivered to the patient and non-irritating to the patient. Typically, base 12 is made of a suitable plastic material that allows some flexibility to conform to the contour of the skin of the patient while being sufficiently rigid to maintain the structural integrity of device 10. Examples of suitable polymers include polyethylene, polypropylene, polystyrene, polyesters, polyamides, polycarbonates, and copolymers thereof.

Embodiment of FIGS. 8–12

Figure 8:
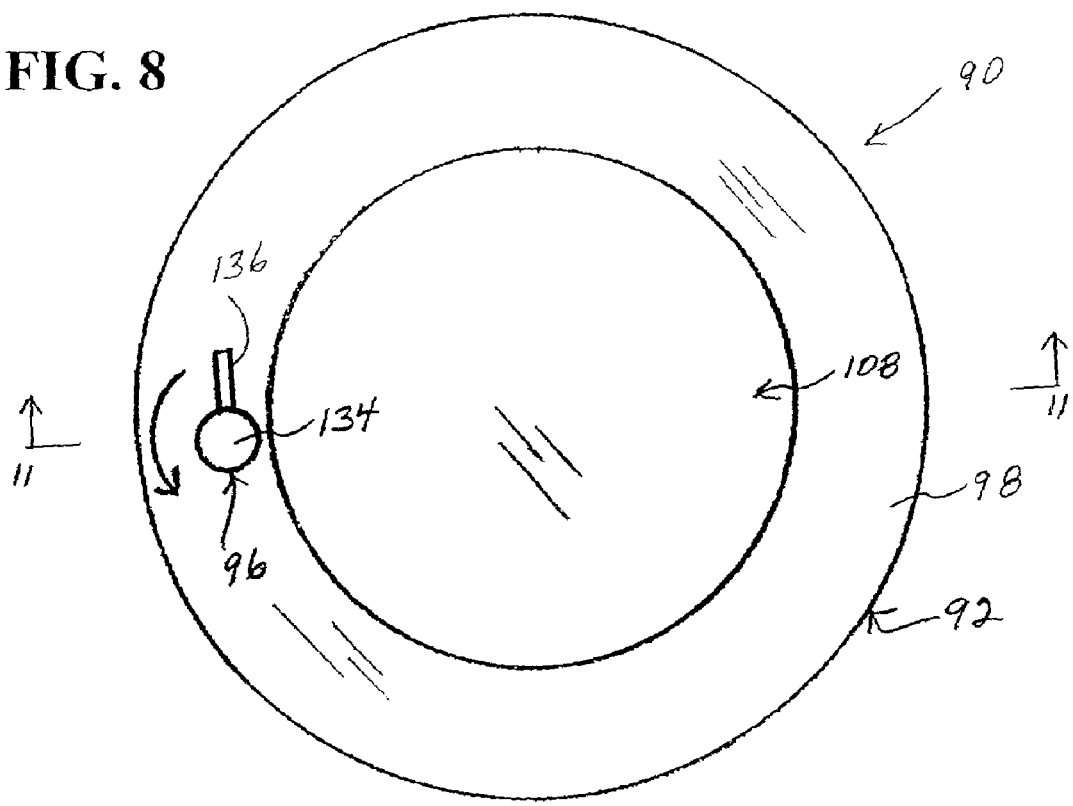
FIG. 8 is a top plan view of a delivery device in a second embodiment of the invention.

Referring to FIGS. 8–12, a second embodiment of the invention is illustrated for delivering a substance intradermally to a patient. Device 90 includes a body 92, a skin penetrating device 94 and a valve assembly 96. As shown in FIG. 8, body 92 has a generally circular configuration with a substantially flat planar top surface 98 and a planar bottom surface 100.

Figure 9:
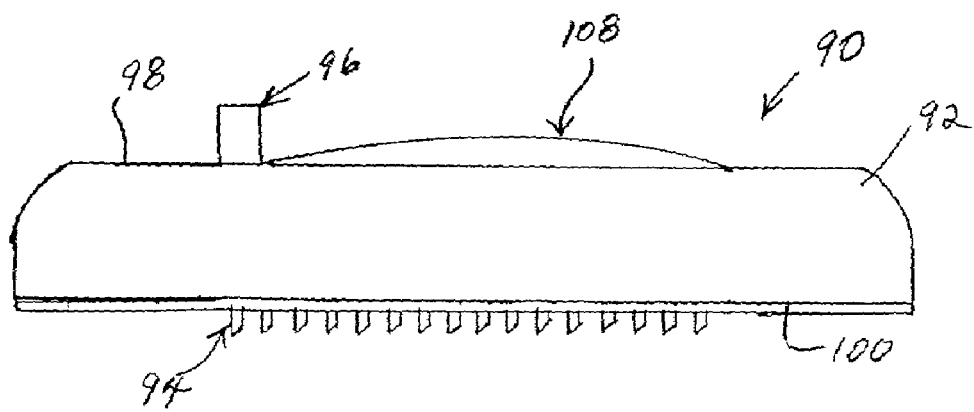
FIG. 9 is a side elevational view of the device of FIG. 8.

Top surface 98 of body 92 includes a recess 102 defined by a bottom surface 104 and a side wall 106. A flexible closure member 108 is coupled to top face 98 to close recess 102. Closure member 108 defines a reservoir having a chamber 110 between bottom surface 104 and closure member 108. As shown in FIG. 9, closure member 108 has a generally hemispherical shape having a convex top surface 112 and a concave bottom surface 114. A movable dispensing member is in the form of a closure member 108, which is preferably made of a material having the same characteristics as the material of the movable dispensing member 52 of the embodiment of FIGS. 1–7. In this embodiment, closure member 108 forms a top wall of chamber 110 and covers an area at least equal to the area of recess 102.

Figure 11:
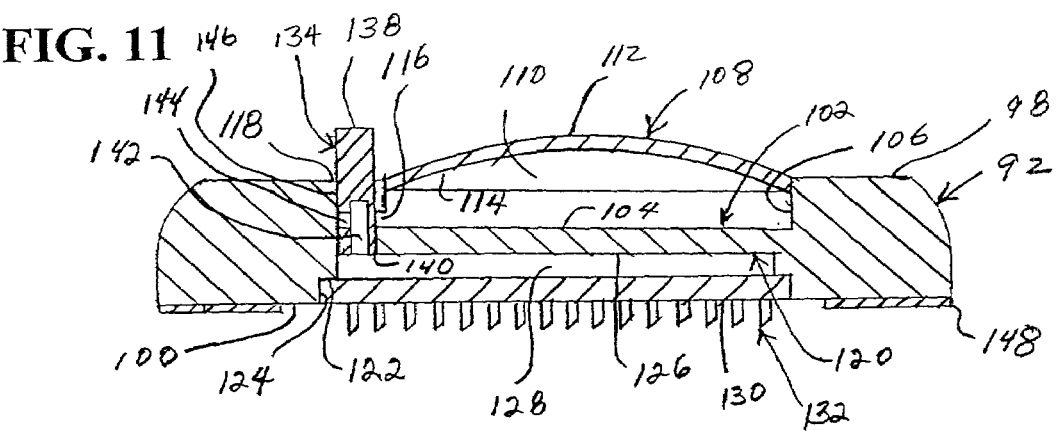
FIG. 11 is a cross-sectional side view of the skin penetrating device taken along line 11—11 of FIG. 8 showing the reservoir filled with a substance.
Figure 12:
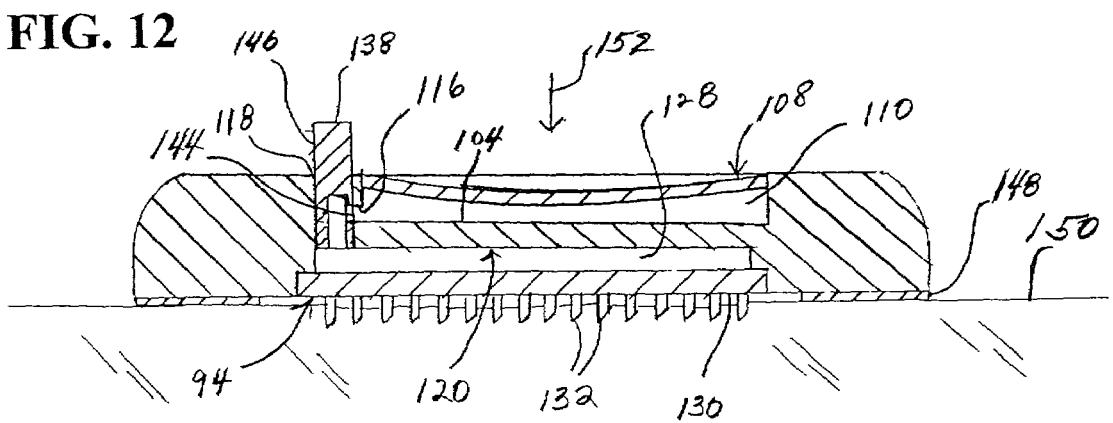
FIG. 12 is a cross-sectional view of the device of FIG. 8 showing the device penetrating the skin and the top wall depressed to dispense the substance.

Side wall 106 of recess 102 includes a channel 116 extending radially outward from side wall 106. An aperture 118 defining a cylindrical channel extends between top surface 98 of body 92 and bottom surface 100. As shown in FIG. 11, channel 116 intersects with aperture 118.

Bottom surface 100 of body 92 includes a recess 120 dimensioned to receive skin penetrating device 94. Recess 120 includes a ledge 122 having a side wall 124 for receiving skin penetrating device 94. As shown in FIG. 11, side wall 124 has a height corresponding substantially to the thickness of skin penetrating device 94, so that the outer face of skin penetrating device 94 lies in the plane of bottom surface 100 of body 92.

Recess 120 has a bottom surface 106 that is spaced from bottom surface 100 by a distance greater than the thickness of skin penetrating device 94 to define a cavity 128. Aperture 118 communicates with cavity 128 to provide fluid communication between chamber 110 and cavity 128.

Skin penetrating device 94 includes a base 130 having at least one micro skin penetrating member 132 extending outwardly therefrom. As shown in FIG. 11, base 130 is dimensioned to fit on ledge 122 of recess 120. Micro skin penetrating members 132 are preferably microneedles in an array, the members each having a length sufficient to penetrate the surface of the skin to a selected depth for delivering a substance into the skin to a depth at which the substance can be utilized by the body.

Valve assembly 96 includes a cylindrical element body 134 dimensioned to fit in aperture 118. An actuating handle 136 is coupled to a top end 138 of valve body 134. Valve body 134 has a bottom end 140 with an axial passage 142.

A radial passage 144 extends through a side face 146 of valve body 134 and intersects with axial passage 142. As shown in FIG. 11, radial passage 144 is aligned with channel 116. Valve body 134 can be rotated within aperture 118 between the closed position of FIG. 11 and the open position of FIG. 12, the handle 136 indicating the position fo the valve. Valve body 134 effectively closes chamber 110 to contain the substance within chamber 110 during storage and shipping of device 90. Valve body 134 can be rotated to the open position of FIG. 12 to provide fluid communication between chamber 110 and cavity 128.

Figure 10:
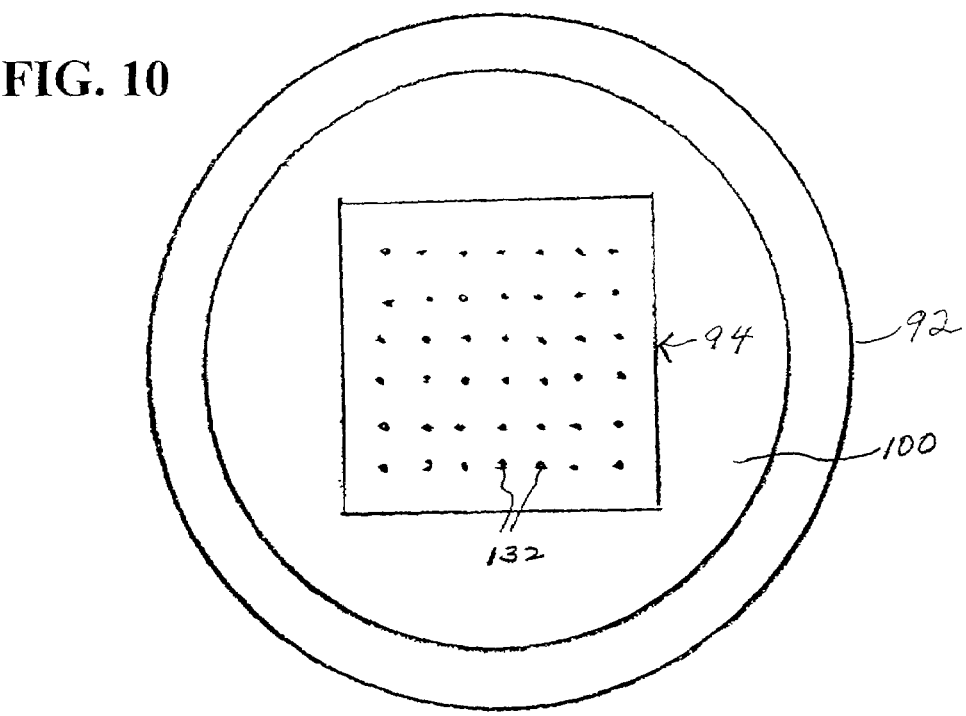
FIG. 10 is a bottom plan view of the device of FIG. 8.

Device 90 is used in a manner similar to the embodiment of FIGS. 1–7. Bottom surface 110 in the embodiment illustrated has an adhesive 148 such as a pressure-sensitive adhesive around the peripheral edge of body 92. As shown in FIG. 10, adhesive 148 surrounds skin penetrating device 94. Device 90 is positioned on the skin 150 of a patient and pressed downwardly to enable micro skin penetrating members 132 to penetrate the skin 150 and to allow adhesive 148 to attach device 190 to skin 150. Valve body 134 is rotated to the open position to provide fluid communication between chamber 110 and cavity 128. A downward pressure indicated by arrow 152 is applied to closure member 108 to produce a dispensing pressure sufficient to deliver a substance intradermally to the patient.

Embodiment of FIGS. 13–19

FIGS. 13–19 show another embodiment of a device 160 for delivering a substance intradermally to a patient. Device 160 includes a housing 162, a skin penetrating device 164 and a valve element or body 166.

Figure 13:
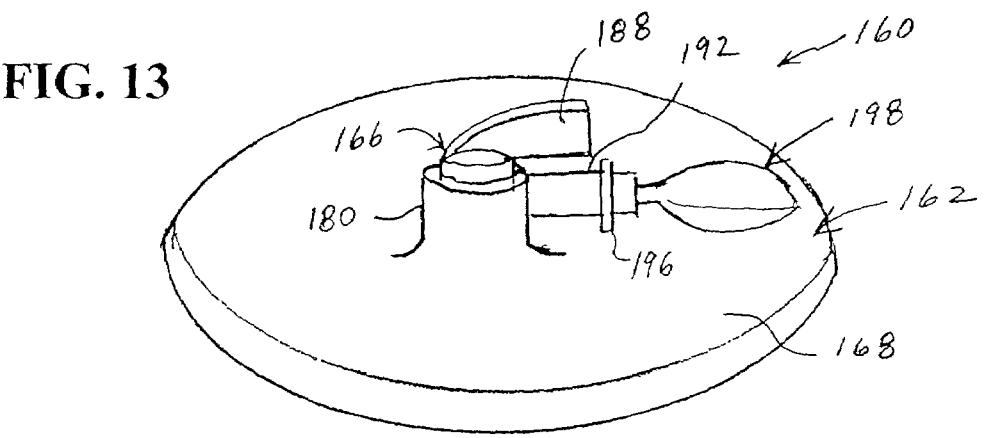
FIG. 13 is a perspective view of the device in another embodiment of the invention.
Figure 14:
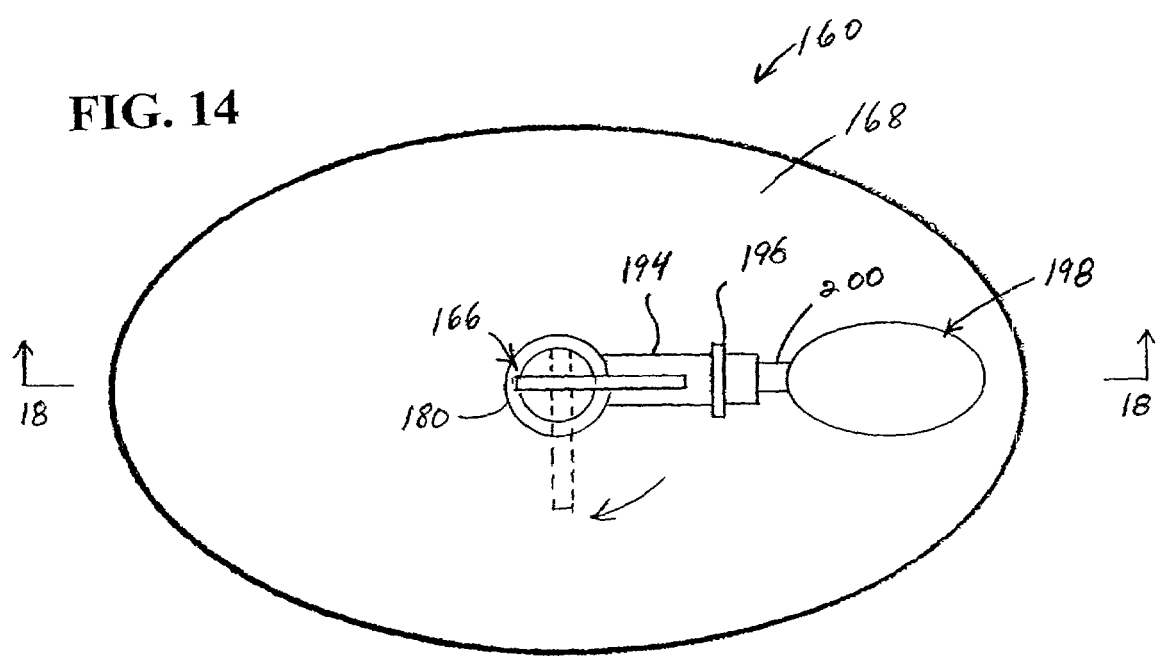
FIG. 14 is a top plan view of the device of FIG. 13.
Figure 15:
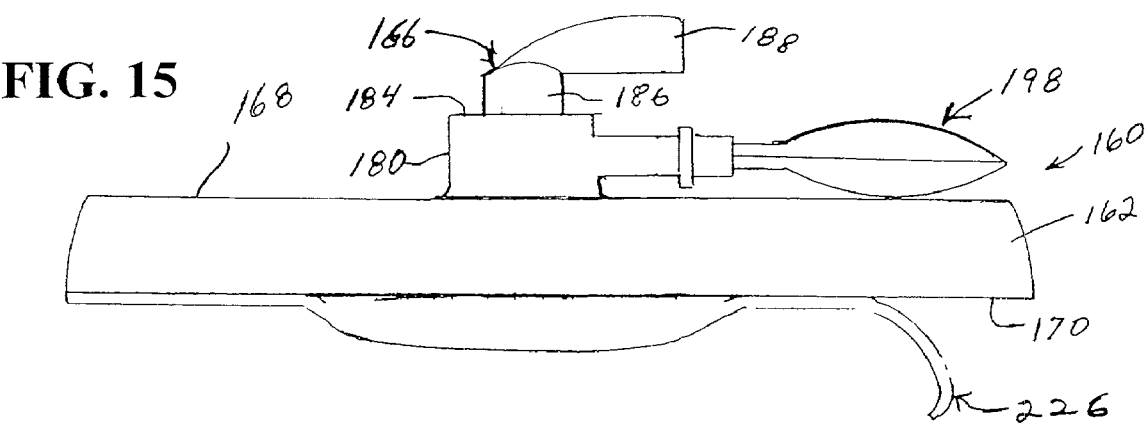
FIG. 15 is a side view of the device of FIG. 13 showing a protective strip partially removed from the device.
Figure 16:
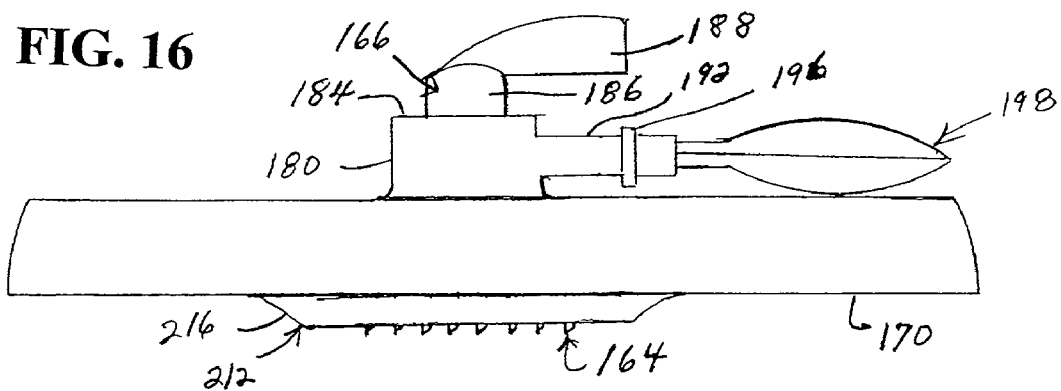
FIG. 16 is a side view of the device of FIG. 13 showing the rib around the micro skin penetrating members.

Housing 162, as shown in the embodiment of FIGS. 13 and 14, has a substantially oval shape, a planar top surface 168 and a bottom surface 170. Bottom surface 170 includes a recess 172 having a ledge 174 and a side wall 176. As in the previous embodiments, ledge 174 and side wall 176 are dimensioned to support skin penetrating device 164. Recess 172 is dimensioned to form an internal cavity 178 communicating with skin penetrating device 164. Valve body 166 is mounted on housing 162 for controlling the flow of liquids into cavity 178. In this embodiment, valve body 166 includes a collar 180 coupled to top surface 168 of housing 162. Collar 180 has a substantially annular shape with an axial passage 182. Axial passage 182 extends from a top end 184 of collar 180 to cavity 178. A cylindrical valve body 186 fits in axial passage 182 and is rotatable within collar 180. An actuating handle 188 is coupled to a top end 190 of valve body 186. Handle 188 is positioned for rotating valve body 186 about the longitudinal axis of collar 180.

A supply tube 192 is coupled to collar 180 and extends radially outward from collar 180 in a direction generally parallel to top surface 168 of housing 162. Supply tube 192 includes an axial passage 194 extending radially through collar 180 and intersecting axial passage 182 of collar 180. Supply tube 192 has an outer end with a coupling member 196 for removably coupling a supply device or container 198 to the delivery device 160.

Supply device 198 is removably coupled to coupling member 196. Coupling member 196 can be a luer-type fitting, friction fit or other suitable coupling member capable of forming a fluid coupling with supply device 198.

Supply device 198 is preferably a single use disposable device containing a unit dose of the substance to be delivered to the patient. In the embodiment illustrated, supply device 198 includes a collar 200 and a compressible hollow body 202 containing the substance to be delivered to the patient. Collar 200 complements coupling member 196 for coupling supply device 198 to device 160. In the embodiment illustrated, body 202 is a bladder formed from a flexible material that can be compressed to dispense the contents of supply device 198. In other embodiments, supply device 198 can be a commercially available device containing a predetermined unit dose of a substance to be delivered and being squeezable to deliver the substance. One such device is sold under the trademark UNIJECT by Becton Dickinson and Company. Other unit dose delivery devices can be used instead.

Figure 17:
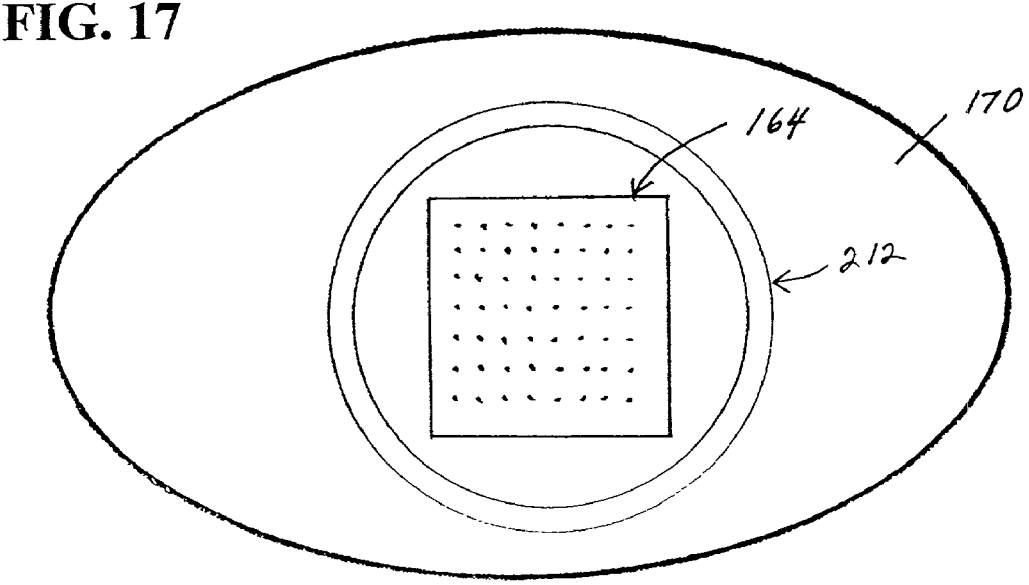
FIG. 17 is a plan bottom view of the device of FIG. 13.
Figure 18:
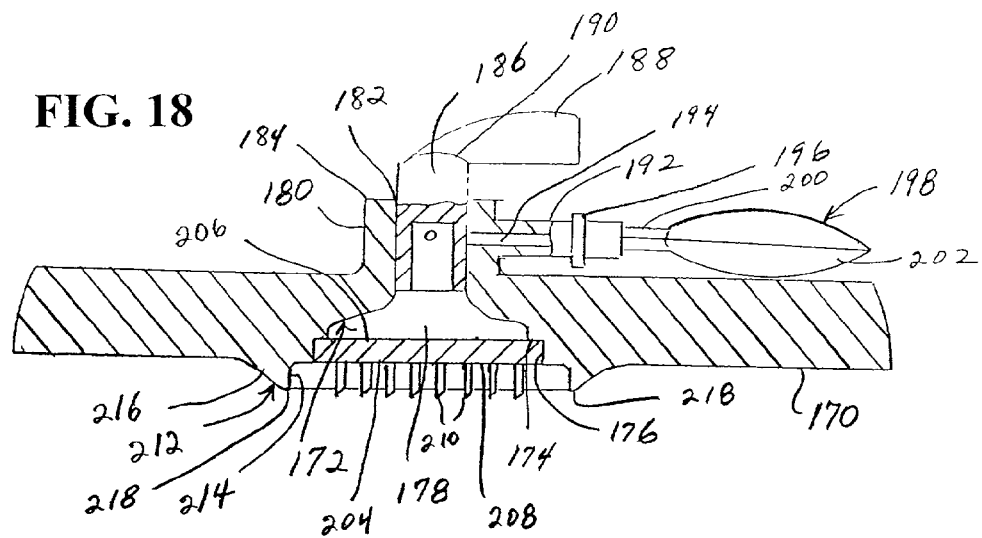
FIG. 18 is a cross-sectional view taken axially to the line of 18—18 of FIG. 14.

As in the previous embodiments, skin penetrating device 164 includes a base 202 having a top face 206 and a planar bottom face 208. At least one micro skin penetrating member 210 in the form of a microneedle extends outwardly from bottom face 208. Micro skin penetrating members 210 have an axial passage extending between top face 206 in communication with cavity 178 and the tip of skin penetrating member 210. Bottom surface 170 of body 162 includes a rib 212 extending outwardly from body 162. Rib 212 surrounds skin penetrating device 164 and has a substantially annular shape as shown in FIG. 17. In the embodiment illustrated, rib 212 has an inner face 214 extending generally perpendicular to bottom face 170 of body 162. Rib 212 also includes an outer face 216 converging toward inner face 214 to form a crest 218. Outer face 216 is formed at an incline with respect to bottom face 170.

In the embodiment illustrated, rib 212 is spaced outwardly from micro skin penetrating members 210 and is impressed on the skin to define a target area on the skin for the micro skin penetrating members 210. Preferably, micro skin penetrating members 210 have an axial length slightly greater than the height of rib 212 as shown in FIG. 19.

Device 160 is placed on the skin 220 of a patient and pressed downwardly. The downward pressure on device 160 causes rib 212 to contact skin 220 and stretch the skin in a target area 222 surrounded by rib 212. Stretching the skin in target area 222 enables micro skin penetrating members 210 to pierce the surface of the skin. The normal elasticity of the skin provides a penetrating resistance to micro skin penetrating members 210. By stretching the skin in the target area 222, micro skin penetrating members 210 are better able to pierce the surface of the skin. In addition, rib 212 forms a seal against the surface of skin 220 to contain the substance that can leak from target area 222.

Figure 19:
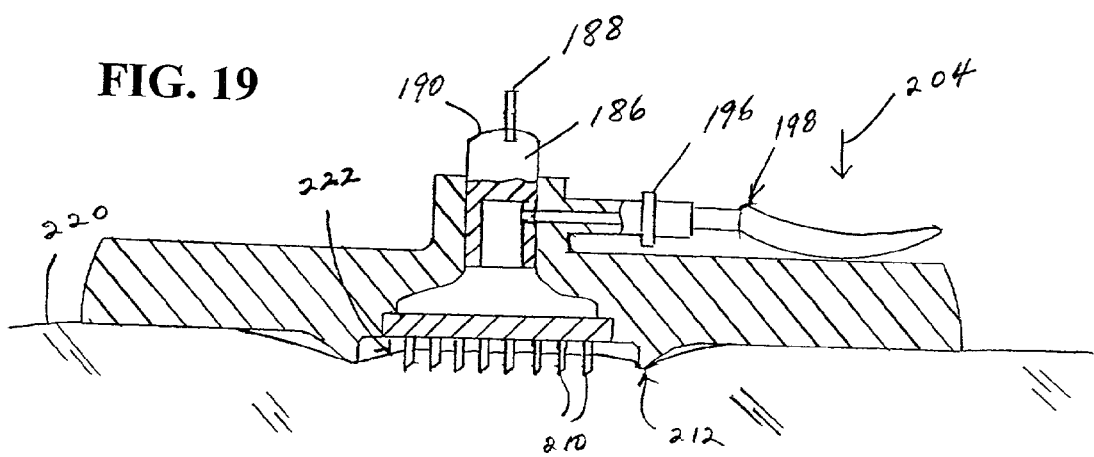
FIG. 19 is a cross-sectional view similar to FIG. 13, but showing the device in contact with the skin of a patient and the device delivering the substance through the micro skin penetrating members.

After device 160 is positioned on skin 220, valve body 166 is rotated to the open position shown in FIG. 19, the position fo the handle 188 indicating the position of the valve body 166. A dispensing pressure indicated by arrow 224 is provided on supply device 198 to dispense the contents of supply device 198 through axial passage 194 and into cavity 178 where the substance can be delivered to micro skin penetrating members 210. Preferably, supply device 198 is able to provide a pressure sufficient to dispense the contents and deliver the contents through micro skin penetrating members 210 into the skin of the patient. After the contents of supply device 198 is delivered to the patient, device 160 is separated from skin 220 and discarded.

Device 160 is preferably designed and constructed to be a disposable, single use device. The device is prepackaged in a sterile condition for immediate use. In the illustrated embodiment, bottom face 170 of body 162 includes a protective cover sheet 226. Cover sheet 226 is attached to bottom surface 170 in a manner that can be peeled easily from device 160 at the time of use. Cover sheet 226 is preferably a flexible sheet material such as Tyvek®. Cover sheet 226 has a dimension to cover skin penetrating device 164 to maintain skin penetrating device 164 in sterile conditions until use. Cover sheets similar to cover sheet 226 can be used in connection with other embodiments according to the present invention.

The illustrated embodiments of the device can be used safely and effectively for the intradermal delivery of a pharmaceutical agent or other substance to a patient. The device is particularly suitable for introducing a vaccine intradermally for efficiently delivering a small amount of a vaccine antigen. The length, width and spacing of the microneedles can vary depending on the pharmaceutical agent being administered and the desired depth of penetration for delivery. When delivering a vaccine, the microneedles are dimensioned to target the optimum intradermal delivery site to promote the desired immune response.

While several exemplary embodiments have been chosen to illustrate the invention, it will be appreciated by those skilled in the art that various additions and modifications can be made to the invention without departing from the scope of the invention as defined in the appended claims.

What is claimed is:

1. An intradermal delivery device for delivering a substance into the skin of a patient, comprising:
   a housing;
   a fluid chamber on the housing for containing the substance, said chamber having an outlet for the substance;
   a manually actuatable valve member connected to said housing to control the flow of the substance through the outlet, wherein the valve member has a portion exposed to the exterior of the device for digital manipulation between a closed position in which the substance is physically prevented from flowing through the outlet and an open position in which the substance is permitted to flow through the outlet; and
   a skin penetrating device on the housing and in fluid communication with the chamber for selectively delivering the substance into the skin of the patient wherein the skin penetrating member has a length of from about 50 microns to about 4,000 microns.

2. The intradermal delivery device of claim 1, wherein said valve member is integrally formed with said housing.

3. The intradermal delivery device of claim 1, wherein said housing includes a cavity communicating with the outlet of said chamber, and said skin penetrating device communicates with said cavity.

4. The intradermal delivery device of claim 3, wherein said skin penetrating device comprises at least one skin penetrating member having a passage through which the substance can flow, the passage having an inlet in fluid communication with said cavity.

5. The intradermal delivery device of claim 3, wherein said skin penetrating device comprises a plurality of spaced skin penetrating members, each of said skin penetrating members having a passage through which the substance can flow, each passage having an inlet in fluid communication with said cavity.

6. The intradermal delivery device of claim 1, wherein said skin penetrating device comprises at least one skin penetrating member having a passage through which the substance can flow, the passage having an inlet in fluid communication with said chamber.

7. The intradermal delivery device of claim 6, wherein said skin penetrating device comprises a plurality of spaced skin penetrating members, each of said skin penetrating members having a passage through which the substance can flow, each passage having an inlet in fluid communication with said chamber.

8. The intradermal delivery device of claim 1, wherein said chamber comprises a reservoir sized to be completely filled by a unit dose of the substance.

9. The intradermal delivery device of claim 1, further comprising a movable member for applying sufficient fluid pressure to the fluid chamber to deliver the substance into the skin of a patient.

10. The intradermal delivery device of claim 9, wherein said movable member is a deformable member defining at least a portion of said fluid chamber, whereby deformation of said deformable member produces a dispensing pressure on the chamber.

11. The intradermal delivery device of claim 8, wherein said housing includes a flexible top wall and a substantially rigid bottom wall defining said reservoir therebetween, said top wall being deformable to produce a dispensing pressure on said reservoir.

12. The intradermal delivery device of claim 1, wherein the fluid chamber comprises a supply container removably coupled to the housing.

13. The intradermal delivery device of claim 12, wherein the supply container contains a unit dose of the substance to be delivered.

14. The intradermal delivery device of claim 1, wherein the fluid chamber contains a unit dose of the substance to be delivered.

15. The intradermal delivery device of claim 1, wherein said housing includes a bottom face, and said skin penetrating device is coupled to said bottom face, said bottom face having a rib surrounding said skin penetrating device for impressing a containment area in the skin of a patient, around a target area on the skin.

16. The intradermal delivery device of claim 1, wherein said portion has a handle.

17. The intradermal delivery device of claim 1, wherein said housing includes a cavity communicating with the outlet of said chamber, and said skin penetrating device communicates with said cavity.

18. The intradermal delivery device of claim 17, wherein the valve element is positioned between said cavity and the outlet of the fluid chamber.

19. The intradermal delivery device of claim 18, wherein said valve element is rotatable between said open position and said closed position.

20. The intradermal delivery device of claim 3, wherein the cavity in said housing includes a bottom face, a recess in said bottom face, and said skin penetrating device is mounted in said recess to define the cavity between said skin penetrating device and said bottom face of said recess.

21. The intradermal delivery device of claim 1, wherein said fluid chamber is prefilled with the substance.

22. The intradermal delivery device of claim 1, wherein said fluid chamber is prefilled with a unit dose of the substance.

23. The intradermal delivery device of claim 9, wherein said housing includes a top wall and a bottom wall defining said reservoir therebetween.

24. The intradermal delivery device at claim 23, wherein said top wall includes said movable member.

25. The intradermal delivery device of claim 24, wherein said movable member is made of a flexible material.

26. The device of claim 25, wherein said flexible material is resilient.

27. The intradermal delivery device of claim 1, wherein said fluid chamber is integrally formed with said housing.

28. The intradermal delivery device of claim 4, wherein the skin penetrating member has a length of from about 50 microns to about 1,500 microns.

29. The intradermal delivery device of claim 4, wherein the skin penetrating member has a length of from about 500 microns to about 1,000 microns.

30. The intradermal delivery device of claim 4, wherein the skin penetrating member is a needle of from about 30 gauge to about 50 gauge.

31. The intradermal delivery device of claim 4, further comprising an adhesive for releasably attaching the device to the skin of a patient.

32. The intradermal delivery device of claim 1, wherein the exposed portion of the valve member comprises an indicator indicating the position of the valve member.

33. The device of claim 4, wherein the skin penetrating member comprises a needle having an axial passage in fluid communication with the fluid chamber for delivering the substance to the patient.

34. An intradermal delivery device for delivering a substance into the skin of a patient, comprising:
    a housing;
    a fluid chamber on the housing for containing the substance, said chamber having an outlet for the substance;
    a manually actualize valve actuator connected to said housing and engaged to a valve disposed within the housing to control the flow of the substance through the outlet, wherein the valve actuator has a portion exposed to the exterior of the device for digital manipulation between a closed position in which the substance is physically prevented from flowing through the outlet and an open position in which the substance is permitted to flow through the outlet; and
    a skin penetrating device on the housing and in fluid communication with the chamber for selectively delivering the substance into the skin of the patient wherein the skin penetrating member has a length of from about 50 microns to about 4,000 microns.

35. The intradermal delivery device of claim 34, wherein said skin penetrating device comprises at least one skin penetrating member having a passage through which the substance can flow, the passage having an inlet in fluid communication with said chamber.

36. The intradermal delivery device of claim 35, wherein said skin penetrating device comprises a plurality of spaced skin penetrating members, each of said skin penetrating members having a passage through which the substance can flow, each passage having an inlet in fluid communication with said chamber.

37. The intradermal delivery device of claim 34, wherein said chamber comprises a reservoir sized to be completely filled by a unit dose of the substance.

38. The intradermal delivery device of claim 34, further comprising a movable member for applying sufficient fluid pressure to the fluid chamber to deliver the substance into the skin of a patient.

39. The intradermal delivery device of claim 38, wherein said movable member is a deformable member defining at least a portion of said fluid chamber, whereby deformation of said deformable member produces a dispensing pressure on the chamber.

40. The intradermal delivery device of claim 37, wherein said housing includes a flexible top wall and a substantially rigid bottom wall defining said reservoir therebetween, said top wall being deformable to produce a dispensing pressure on said reservoir.

* * * * *